United States Patent [19]

Tersteeg et al.

[11] 4,287,155

[45] Sep. 1, 1981

[54] SAMPLE TRAY AND CARRIER FOR CHEMICAL ANALYZER

[75] Inventors: Glenn E. Tersteeg, Honeoye Falls; Richard R. Harold, Penfield, both of N.Y.

[73] Assignee: Eastman Kodak Company, Rochester, N.Y.

[21] Appl. No.: 159,554

[22] Filed: Jun. 16, 1980

[51] Int. Cl.³ .............................................. G01N 35/04
[52] U.S. Cl. ...................................... 422/64; 141/130; 422/100; 422/104
[58] Field of Search ...................... 422/63, 64, 65, 100, 422/104; 141/130

[56] References Cited

U.S. PATENT DOCUMENTS

| 982,351 | 1/1911 | Cree . | |
|---|---|---|---|
| 3,441,383 | 4/1969 | Moore et al. | 422/64 |
| 3,705,788 | 12/1972 | Kolko et al. | 422/64 |
| 3,883,308 | 5/1975 | Matte | 422/64 |
| 4,170,625 | 10/1979 | Welch | 422/64 |

OTHER PUBLICATIONS

"Kodakery", May 8, 1980, pp. 1 and 8.

Primary Examiner—Ronald Serwin
Attorney, Agent, or Firm—M. S. Sales

[57] ABSTRACT

A tray is adapted to be rotatably mounted on chemical analysis apparatus and to receive a plurality of cups of fluid samples for chemical analysis. The tray is formed of a plurality of discrete arcuate segments independently removable from, and replaceable onto the analysis apparatus to form a circular composite tray when all the segments are present. The tray is provided with a plurality of replaceable metering tips, one per fluid sample cup, which may be radially aligned with the cups. The tray segments are mounted on a carrier which can be removed from the chemical analysis apparatus with all the tray segments as a unit.

3 Claims, 4 Drawing Figures

SAMPLE TRAY AND CARRIER FOR CHEMICAL ANALYZER

CROSS-REFERENCE TO RELATED APPLICATIONS

Reference is made to commonly-assigned U.S. Patent Application Ser. No. 159,564 entitled SLIDE DISTRIBUTOR FOR A CHEMICAL ANALYZER filed in the names of M. Montalto et al on even date herewith.

BACKGROUND OF THE INVENTION

1. Field of the Invention

This invention relates to apparatus for the chemical analysis of biological fluids, and more particularly to apparatus for holding and delivering fluid samples to the analysis apparatus.

2. Description of the Prior Art

In recent years, a number of automated systems have been developed for carrying out quantitative chemical analyses of fluid samples. Most of the commercially available systems utilize liquid reagents and require analyzer equipment having intricate solution handling and transport capabilities. For example, U.S. Pat. No. 3,883,308, to Matte, discloses liquid analysis apparatus in which a plurality of sample containers are carried on a circular support, a plurality of reagent cups are supported on a second circular support, and an aspirator is provided for transferring fluid from a sample container to a selected reagent cup. The bottom portions of the reagent cups are transparent to facilitate a photometric reading through the container.

As an alternative to liquid analysis systems, various essentially-dry analytical elements have been adopted for automated test procedures. Co-assigned U.S. Pat. No. 4,152,390, granted May 1, 1979, discloses apparatus for the automatic continuous analysis of biological fluids in which a fluid sample is metered onto a test slide and is analyzed after incubation. Cups of biological fluid samples are carried on a linearly movable tray. Drops of sample fluid are dispensed onto test slides below the tray through metering tips in the bottom of each cup. The tray is incrementally advanced to align successive cups with the dispensing station.

When an entire tray has been run, it is removed and replaced with a new tray of fresh samples. During removal and replacement of a sample tray, the analysis apparatus operation is interrupted. No provision is made for substituting one or more so called STAT (a commonly used term in medical arts for immediately needed) tests without removing an entire tray.

SUMMARY OF THE INVENTION

In accordance with the present invention, a tray is adapted to be rotatably mounted on chemical analysis apparatus and to receive a plurality of cups of fluid samples for chemical analysis. The tray is formed of a plurality of discrete arcuate segments independently removable from, and replaceable onto the analysis apparatus to form a circular composite tray when all the segments are present. While the analysis apparatus continues to operate on fluid samples carried by one of the tray segments, other segments may be removed to be reloaded with fresh samples, or to insert STAT samples for immediate testing without interruption of the operation.

In a preferred embodiment of the present invention, the tray is provided with a plurality of disposable metering tips, one per fluid sample cup, which may be radially aligned with the cups. The tray segments are mounted on a carrier, which can be removed from the chemical analysis apparatus together with all the tray segments as a composite unit.

The invention is particularly suitable for use in performing analyses of blood sera in which the serum is dispensed onto a test element or a test slide, of the type which is formed as a multi-layer element containing the necessary reagents for reaction with components or the serum. However, the invention is not limited to use with such test elements or slides. Nor is it limited to the analysis of blood sera, and other fluids can be used with apparatus of the type disclosed.

BRIEF DESCRIPTION OF THE DRAWINGS

In the detailed description of the preferred embodiment of the invention presented below reference is made to the accompanying drawings in which.

DESCRIPTION OF THE PREFERRED EMBODIMENT

The slide tray and carrier disclosed herein is particularly useful with high-speed analyzers as shown in commonly-assigned U.S. Patent application Ser. No. 159,564 entitled SLIDE DISTRIBUTOR FOR A CHEMICAL ANALYZER filed in the names of M. Montalo et al on even date herewith. Such analyzers are adapted to process a large number of planar slides containing dry reagents by depositing a predetermined amount of fluid sample on the slide at a metering station. The slides may take various forms, such as for example so-called potentiometric type and colorimetric type analysis slides.

Potentiometric type slides comprise a pair of planar electrodes selective to the ion activity of choice. An example of such a slide is disclosed in U.S. Pat. No. 4,053,381, granted on Oct. 11, 1977 to Hamblen et al. This patent describes a test element, or analysis slide, of the type which is used to potentiometrically designate the activity of ions in a liquid test solution.

A colorimetric type slide is disclosed in commonly-owned U.S. Pat. No. 3,992,158, granted on Nov. 16, 1976 to Przbylowicz et al. That slide is formed as a multi-layered element containing the necessary reagents for reaction with components of a biological fluid, such as blood serum, deposited thereon. Certain reactions colormetrically produce a change in optical density in the element which is sensed by a reflectometer, the amount of light reflected from the element varying in accordance with the reaction and being indicative of the amount of a particular analyte present in the fluid.

Figure 1:
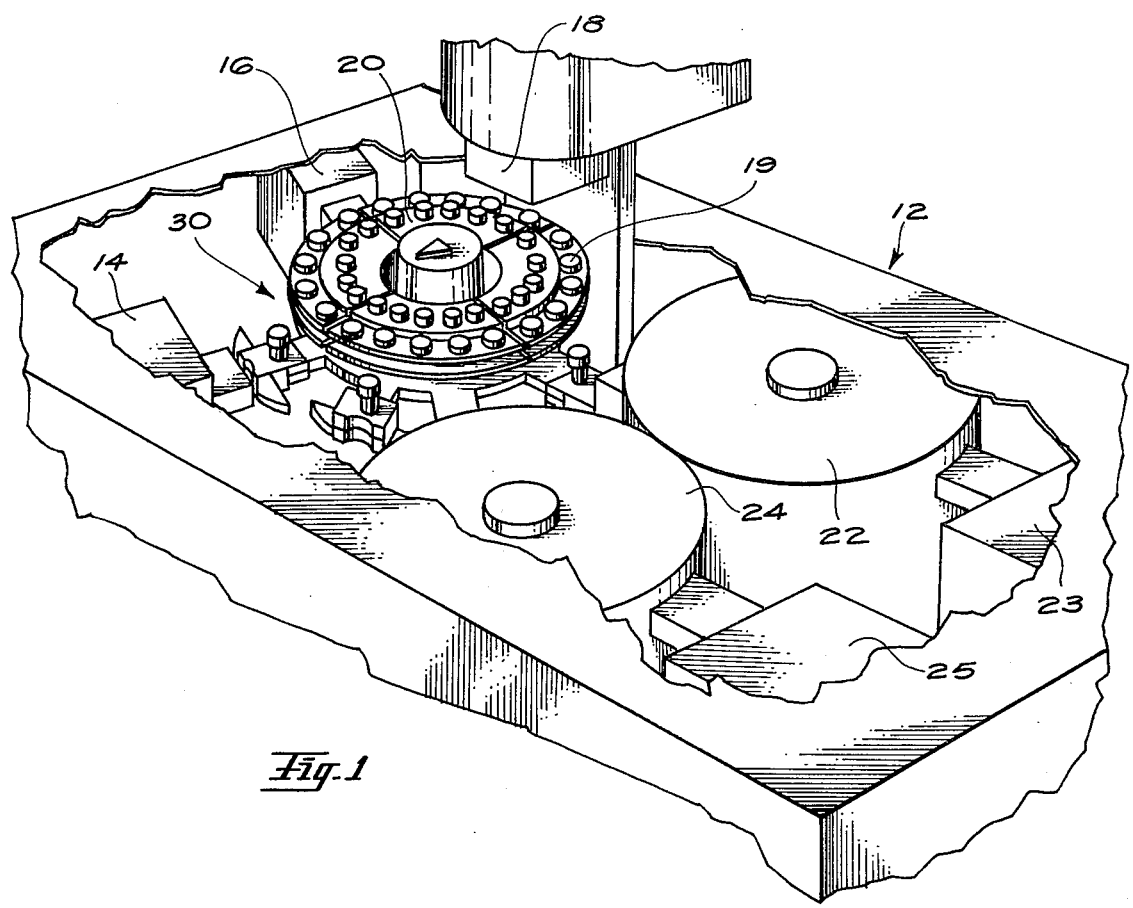
FIG. 1 is a perspective view of a chemical analyzer of the type which is adapted to employ the sample tray and carrier described herein.
Figure 2:
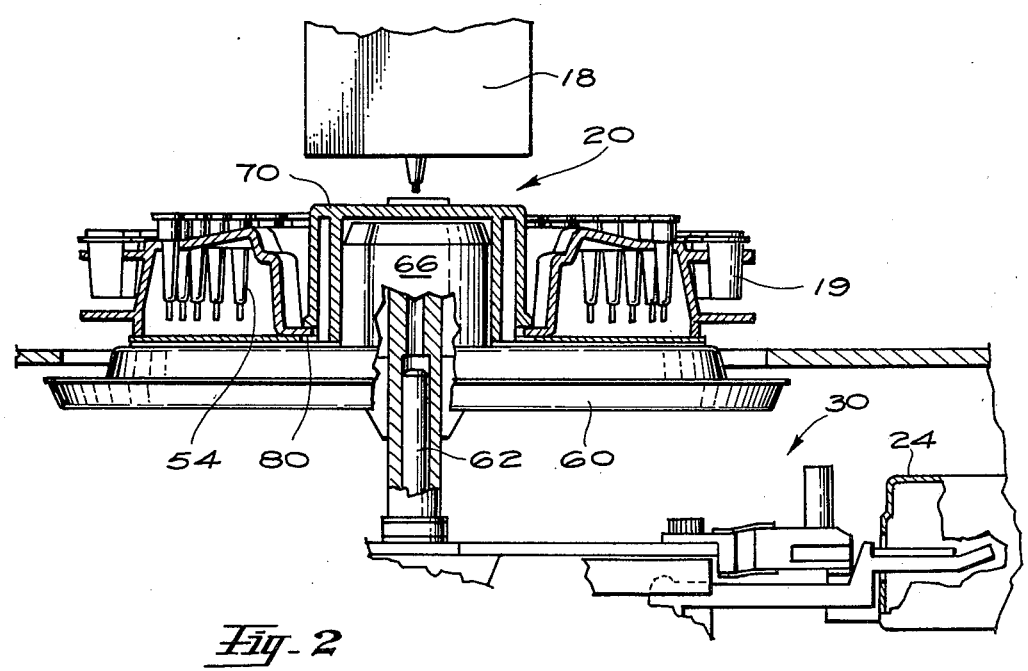
FIG. 2 is a fragmentary elevational view, partially in section of a portion of the chemical analyzer of FIG. 1 and of the sample tray and carrier.

Referring to FIGS. 1 and 2, an analyzer 12 includes a slide supply 14 for analysis slides of the colorimetric type and a slide supply 16 for analysis slides of the potentiometric type. A metering device 18 is adapted to meter fluid sample from a cup 19 in sample tray 20 onto an analysis slide. A second metering device, not shown, works in conjunction with metering device 18 to also deposit reference fluid on potentiometric type analysis slides. After the metering operation, slides of the potentiometric type are delivered to an incubator 22, and analysis slides of the colorimetric type are delivered to an incubator 24. Incubators 22 and 24, are adapted to cooperate respectively with analysis means 23 and 25 of FIG. 1 for measuring changes in the analysis slides as a result of the fluid deposited thereon.

Additional details of analyzer 12 are disclosed in aforementioned U.S. Patent application Ser. No. 159,564 to Montalto et al, and that disclosure is specifically incorporated herein by reference. Briefly, however, a slide distributor 30 receives colorimetric-type slides from supply 14 and potentiometric-type slides from supply 16 and transfers the slide to metering device 18 and incubators 22 and 24.

Figure 3:
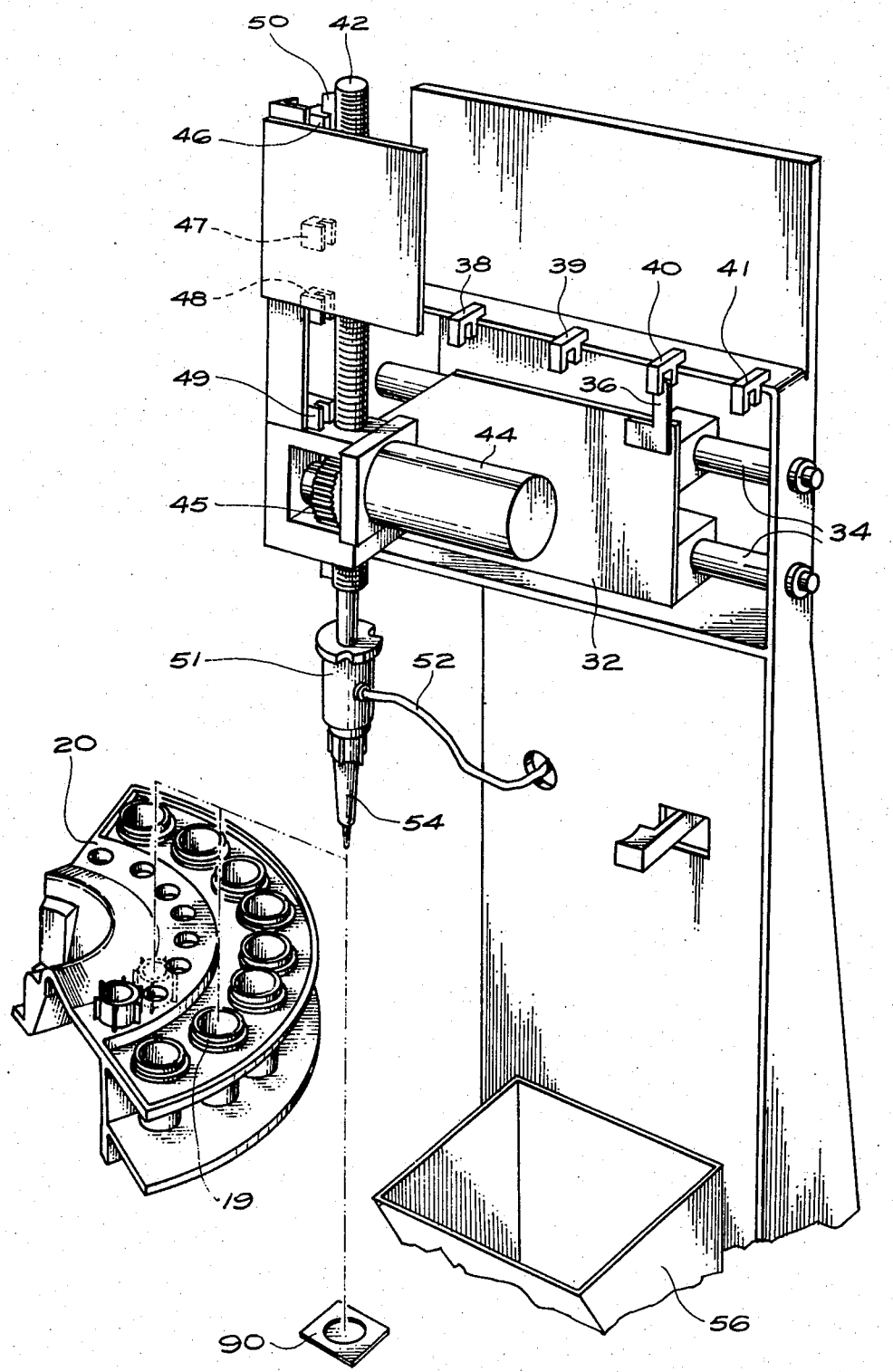
FIG. 3 is a perspective view of a fluid metering device and of a portion of the sample tray.

Metering device 18 is shown schematically in FIG. 3, and includes a carriage 32 slidably mounted for fore and aft movement on a pair of rods 34. A flat 36 passes through four sensors 38–41 to provide an indication of the carriage position at the sensors. A shaft 42 is vertically movable on carriage 32 by a motor 44 and pinion 45. Four position sensors 46–49 detect the height of the shaft by means of a flag 50 carried by the shaft. At the lower end of shaft 42, a coupling 51 is connected to a selectively operable vacuum source, not shown, by a tube 52. The coupling has a depending member, not shown, with an outer diameter such that it will releasably grip the inner wall of disposable metering tips 54 discussed in greater detail hereinafter. A disposal box 56 for the tips is positioned under the path of coupling 51.

Figure 4:
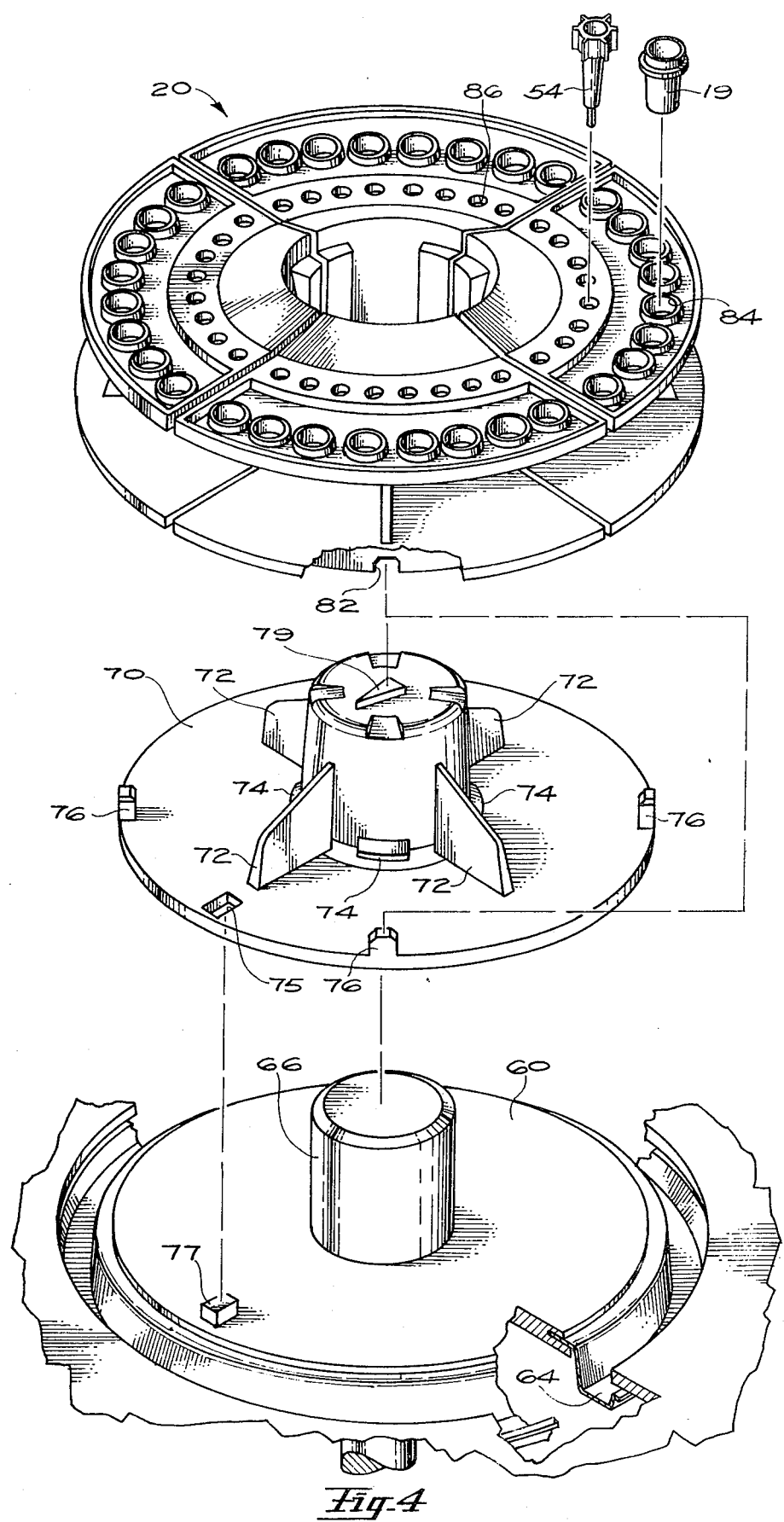
FIG. 4 is an enlarged exploded view of a portion of the chemical analyzer of FIGS. 1 and 2 with the carrier and sample tray shown in greater detail.

Referring to FIGS. 2 and 4, a support 60 is mounted on an indexable shaft 62 for rotation therewith. The support has an upwardly facing trough 64 for catching any spills from sample tray 20. A cylindrical projection 66 extends upwardly from the support and removably receives a circular carrier 70.

The carrier, best seen in FIG. 4, has four radial splines 72 equally spaced around a central hub. Four lips 74 project from the hub between the splines, and four tabs 76 extend from the carrier's base. A hole 75 in the carrier's base is adapted to fit over a key 77 on tray 60 for proper alignment of the carrier with the support. An arrow head 79 on the top of the carrier's central hub aids the operator in aligning hole 75 and key 77.

Sample tray 20 is mountable on carrier 70. The tray comprises four discrete segments which fit between splines 72 on carrier 70. To mount a segment of tray 20, its inner, lower edge 80 (FIG. 2) is inserted under carrier lip 74 and the segment is lowered onto the carrier base, whereat one of tabs 76 fits into a recess 82 in the bottom of the segment.

Each segment has a plurality of discontinuities adapted to be loaded with fluid sample cups 19. In the illustrated embodiment, the cups are loaded in tapered holes 84 around the periphery of the tray. Radially aligned with holes 84, a second set of discontinuities (again tapered holes) 86 are adapted to be loaded with metering tips 54.

The metering tips are hollow needle-like tubes with open ends to be used for sucking or drawing fluid samples from cups 19. Tips 54 have a plurality of ribs 88 around their upper ends so that the tips can be knocked off of coupling 51.

Operation

Generally, an attendant or lab technician, prepares a complete sample tray 20 for testing by inserting four tray segments on a carrier 70. Fresh metering tips 54 are loaded into holes 86 and cups 19 of individual fluid samples are placed in numbered holes 84. A record (preferably computerized) is kept of the location of the samples so that the test results can be matched with the patient. The complete carrier and tray is carried to the analyzer and loaded onto projection 66.

Briefly, the analyzer operates by indexing shaft 42 to its uppermost position aligning flag 50 with sensor 46. Carriage 32 moves to the left as viewed in FIG. 3 until flag 36 reaches sensor 38. Then shaft 42 is lower to slip coupling 51 into a metering tip 54 (flag 50 is at sensor 47).

The coupling is raised with a tip attached, and carriage 32 backs to align flag 36 with sensor 39. Now tip 54 is aligned with a sample cup 19 and is lowered into the cup (flag 50 aligns with sensor 48) where vacuum in tube 52 draws a sample of fluid into tip 54. The tip is raised and backed into alignment with an analysis slide 90, upon which a quantity of fluid is deposited. The tip is disposed of in box 56 before the process is repeated for the next sample.

Replenishment of metering tips and fluid samples can be accomplished in two ways. First, after all the tips and cups on tray 20 have been used, the entire tray, together with its carrier 70 can be removed and replaced by another tray and carrier. This, of course, requires that operation of the analyzer be interrupted during the reloading operation.

Alternatively, and because the tray is divided into a plurality of discrete segments independently removable from carrier 70, a segment can be removed from the analyzer after its cups have been sampled and during sampling of cups on other tray segments. A tray segment of fresh tips and cups can then be inserted onto carrier 70, all without interruption of the analyzing process.

Another advantage of a segmented tray is the capability of inserting segments containing fluid samples of immediately needed tests (STAT samples) in the operation without waiting for a complete tray to be tested.

Although the invention has been described with particular reference to a preferred embodiment thereof, it will be readily understood that variations and modifications can be effected within the spirit and scope of the invention as described hereinabove and as defined in the appended claims.

We claim:

1. A tray and carrier combination, adapted to be rotatably mounted on chemical analysis apparatus and to receive a plurality of metering tips and cups for fluid samples for chemical analysis; said combination comprising:

a circular carrier adapted to be removably mounted on the chemical analysis apparatus for rotation about an axis;

a tray adapted to be mounted on said carrier and having a plurality of discrete arcuate segments independently removable from and replaceable onto said carrier about said axis;

a plurality of angularly spaced first discontinuities on each of said segments, each of said first discontinuities being adapted to receive a fluid sample cup; and a plurality of second discontinuities on each of said segments for receiving a plurality of metering tips, each of said second discontinuities being associated with a different one of said first discontinuities, whereby one of said segments can be removed from said carrier for restocking with fresh metering tips and fluid sample cups while the analysis apparatus continues to operate on the fluid samples in cups on segments retained on said carrier and whereby said carrier and all the segments may be removed from the analysis apparatus as a unit.

2. A tray as defined in claim 1 wherein:
said first discontinuities are arranged on said composite tray in a circle having a central axis;
said second discontinuties are aligned radially, with respect to said central axis, of their associated first discontinuities.

3. A tray as defined in claim 2 wherein said second discontinuities are radially inward of said first discontinuities.

* * * * *